United States Patent
Padala et al.

(10) Patent No.: US 9,295,553 B2
(45) Date of Patent: Mar. 29, 2016

(54) ANNULOPLASTY RINGS AND METHODS FOR HEART VALVE REPAIR

(75) Inventors: Sai Muralidhar Padala, Atlanta, GA (US); Ajit P. Yoganathan, Tucker, GA (US); Vinod H. Thourani, Atlanta, GA (US); Jorge H. Jimenez, Atlanta, GA (US)

(73) Assignees: Georgia Tech Research Corporation, Atlanta, GA (US); Emory University, Atlanta, GA (US)

(*) Notice: Subject to any disclaimer, the term of this patent is extended or adjusted under 35 U.S.C. 154(b) by 794 days.

(21) Appl. No.: 12/937,191

(22) PCT Filed: Apr. 7, 2009

(86) PCT No.: PCT/US2009/039777
§ 371 (c)(1),
(2), (4) Date: Dec. 17, 2010

(87) PCT Pub. No.: WO2009/126629
PCT Pub. Date: Oct. 15, 2009

(65) Prior Publication Data
US 2013/0030523 A1 Jan. 31, 2013

Related U.S. Application Data

(60) Provisional application No. 61/043,525, filed on Apr. 9, 2008.

(51) Int. Cl.
*A61F 2/24* (2006.01)

(52) U.S. Cl.
CPC .............. *A61F 2/2448* (2013.01); *A61F 2/24* (2013.01); *A61F 2/2409* (2013.01); *A61F 2/2442* (2013.01);
(Continued)

(58) Field of Classification Search
CPC ....................... A61F 2/2442; A61F 2230/0095

USPC .................................................. 623/2.36–2.37
See application file for complete search history.

(56) References Cited

U.S. PATENT DOCUMENTS 4,917,698 A 4/1990 Carpentier et al.
5,776,189 A 7/1998 Khalid
(Continued)

FOREIGN PATENT DOCUMENTS

JP 2007512919 5/2007
WO 2005055883 A1 6/2005
(Continued)

OTHER PUBLICATIONS

Japanese Notice of Reasons for Final Rejection dated Apr. 22, 2014 cited in Application No. 2011-504127, 9 pgs.
(Continued)

*Primary Examiner* — Jacqueline Woznicki
(74) *Attorney, Agent, or Firm* — Merchant & Gould P.C.

(57) ABSTRACT

An annuloplasty ring, configured for implantation in the annulus of a heart valve, comprising multiple segments each of which are geometrically shaped from a three dimensional perspective to conform to the anatomic shape of the valve annulus. In one embodiment, at least one of the multiple segments of the annuloplasty ring is configured to facilitate a reduction of tension on heart valve tissue and eliminate a substantial portion of potential pressure or force that may be applied to the atrio-ventricular node by the annuloplasty ring when inserted into a heart valve. In another embodiment, at least one of the multiple segments of the annuloplasty ring are configured to include an assembly that facilitates selective adjustment of a segment's respective length and/or shape. The adjustment of the length of one of the ring segment's results in an adjustment of at least one angle between at least one set of other ring segments, thereby causing an adjustment to the geometric characteristics of the ring.

12 Claims, 8 Drawing Sheets

(52) U.S. Cl.
CPC ....... *A61F 2/2445* (2013.01); *A61F 2230/0023* (2013.01); *A61F 2230/0063* (2013.01); *A61F 2230/0095* (2013.01); *A61F 2250/0004* (2013.01)

(56) References Cited

U.S. PATENT DOCUMENTS

| | | | |
|---|---|---|---|
| 6,368,348 | B1 | 4/2002 | Gabbay |
| 6,726,716 | B2 * | 4/2004 | Marquez ................ 623/2.36 |
| 2001/0021874 | A1 | 9/2001 | Carpentier et al. |
| 2003/0045929 | A1 * | 3/2003 | McCarthy et al. .......... 623/2.37 |
| 2005/0131533 | A1 | 6/2005 | Alfieri et al. |
| 2005/0182487 | A1 | 8/2005 | McCarthy et al. |
| 2005/0192666 | A1 | 9/2005 | McCarthy |
| 2007/0005134 | A1 * | 1/2007 | McCarthy ................ 623/2.17 |
| 2007/0016287 | A1 * | 1/2007 | Cartledge et al. .......... 623/2.11 |
| 2007/0027536 | A1 | 2/2007 | Mihaljevic et al. |
| 2008/0015688 | A1 | 1/2008 | Hill et al. |
| 2008/0027483 | A1 | 1/2008 | Cartledge et al. |
| 2008/0058924 | A1 | 3/2008 | Ingle et al. |

FOREIGN PATENT DOCUMENTS

| | | |
|---|---|---|
| WO | 2007136783 A2 | 11/2007 |
| WO | 2009126629 A1 | 10/2009 |

OTHER PUBLICATIONS

Canadian Office Action dated Feb. 18, 2015 cited in Application No. 2,753,027, 3 pgs.
European Communication/Supplementary European Search Report dated Jul. 9, 2015 cited in Application No. 09 7301 18.8, 11 pgs.

* cited by examiner

ANNULOPLASTY RINGS AND METHODS FOR HEART VALVE REPAIR

CROSS-REFERENCE TO RELATED APPLICATIONS

The present application is being filed on 8 Oct. 2010, as a U.S. National Stage of PCT International Patent application No. PCT/US2009/039777, file on 7 Apr. 2009 and claims priority to United States provisional patent application having Ser. No. 61/043,525 titled "ANNULOPLASTY RINGS AND METHODS FOR HEART VALVE REPAIR" filed Apr. 9, 2008, and which applications are incorporated herein by reference. To the extent appropriate, a claim of priority is made to each of the above disclosed applications.

FIELD OF INVENTION

This invention relates to devices and methods for repair of heart valves using invasive and minimally invasive devices. The devices and methods described in the present invention provide effective ways of repairing atrio-ventricular heart valves to reduce or alleviate regurgitation. More particularly the present invention relates to an annuloplasty device that is either completely rigid or has a combination of rigid and flexible components, which can be operatively configured to be manipulated and formed in a shape of a specific patient's tricuspid valve annulus either on a flaccid heart on cardiopulmonary bypass or on a beating heart under visual or image guidance, in order to reduce or alleviate regurgitation of the atrioventricular valve.

BACKGROUND OF THE INVENTION

The heart is a hollow muscular organ with four pumping chambers: the left and right atria and the left and right ventricles. One-way valves between each of the chambers control the flow of blood in and out of the heart. The valves that control the blood flow between the atria and the ventricle are termed as Atrio-Ventricular Valves while the valves between the Ventricles and the outflow tracts are Outflow Tract/Semi-lunar Valves. The left atrio-ventricular valve is called the Mitral Valve, while the left ventricular outflow tract valve is called the Aortic Valve. Similarly, the right atrio-ventricular valve is called the Tricuspid Valve, while the right ventricular outflow tract valve is called the Pulmonary Valve.

Heart failure related to heart valve dysfunction is a widespread condition in which one or more of the heart valves fail to function properly. The dysfunction of the valves is mainly divided into two types: a) Valve Stenosis—wherein the effective flow orifice area of the valve is decreased due to various reasons and there is significant obstruction to the forward flow through the valve and b) Valve Incompetence—wherein the valves do not close properly and there is excessive retrograde leakage of blood when the valve is closed. Both types of these disease lead to debilitating effect on the performance of the heart and could also lead to congestive heart failure.

Surgery to repair damaged valves is the method of choice over valve replacement in the current surgical era. Surgical repair techniques involve reconstruction or controlled alteration of the geometry of the native valve using implantable devices. One of the most common repair technique used today by the surgeons to repair atrio-ventricular valve regurgitation is annuloplasty, in which the valve annulus is geometrically stabilized or reduced in size by suturing a prosthetic annuloplasty ring onto the annulus. The annuloplasty rings are designed to roughly conform to the shape of the annulus and maintain ample leaflet coaptation and allow good forward flow. There are also specific annuloplasty rings that have a non-physiological shape and upon implantation conform to the shape of the atrioventricular valve annulus to their non-physiological shape. These annuloplasty rings are generally made in different shapes, sizes and mechanical properties. D-shaped annuloplasty ring is the most common among the shapes with two important sub-categories being the full ring and a partial ring. The rings are also made rigid, semi-flexible and flexible that claim to allow the restoration of the native valve kinematics.

Implantation of these rings requires surgical intervention with an open-chest and the patient on cardiopulmonary bypass for a significant period. Surgical skill is of utmost importance in creating the sterna incision or thoracotomy and in opening the left atrial wall to provide exposure of the mitral valve. Using current techniques, once the annuloplasty ring is implanted it can neither be changed in shape nor size, and thus choice of the optimal annuloplasty ring type with required geometric characteristics is key for post-operative success. Minimally invasive procedures that can implant annuloplasty rings at the location of interest through less invasive techniques may decrease post-operative risk and reduce the patient mortality.

Figure 1:
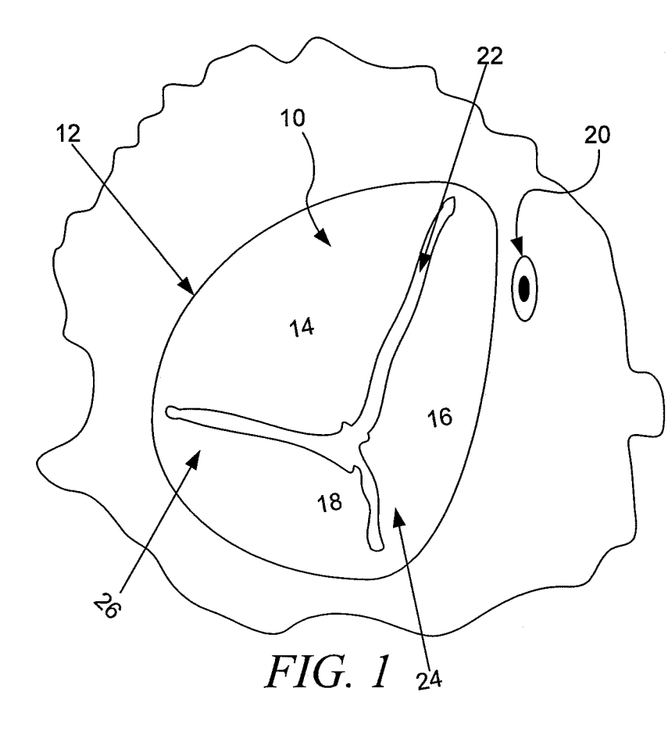
FIG. 1 is a plan view of a tricuspid valve and surrounding anatomy.

The present invention has particular relevance to the repair of dysfunctional tricuspid valves using both invasive and minimally invasive techniques. The tricuspid valve 10 regulates the flow of blood between the right atrium and the right ventricle. The tricuspid valve 12 has three main components—the tricuspid annulus 12, the three leaflets 14, 16, 18 and the three papillary muscles (not shown). The annulus 12 of the valve is a fibro-muscular ring from which the three leaflets 14, 16, 18 (anterior, septal and posterior) originate and regulate the flow through the valve orifice. The leaflets 14, 16, 18 extend inward into the valve or flow orifice defined by the annulus 12. There are three commissures between the three leaflets, which include an anteroseptal commissure 22, a posteroseptal commissure 24 and an anteroposterior commissure 26. Fibrous chordae tendineae extend from the three leaflets 14, 16, 18 and insert into the three papillary muscles extending from the heart muscle. The papillary muscles located in the right ventricle hold the leaflets and restrict them from prolapsing into the right atrium. The tricuspid annulus 12 is an ovoid-shaped fibrous ring, which is not very prominent and is larger in the circumferential area and different in shape than the mitral valve.

Generally, both mitral and tricuspid regurgitation occur simultaneously in a patient. Moreover, in the past tricuspid insufficiency was considered as a silent and almost benign disease which was a subsequent complication of mitral insufficiency, and therefore, if mitral insufficiency was corrected, tricuspid insufficiency would revert by itself. Recent Studies by Matsaguna et. al. 2005 have shown the contrary, even after mitral regurgitation is corrected surgically, tricuspid regurgitation persists and grows with time. The presence of tricuspid insufficiency results in increased mortality and accelerated progression of heart failure in a significant patient population. Therefore, there is a significant need to create devices and procedures which may correct tricuspid regurgitation.

Currently most atrioventricular valve repair technologies are tailored to repair the mitral valve, since this valve is generally more susceptible to disease. Therefore, it is commonplace to use annuloplasty rings designed for the mitral valve in the tricuspid position. Since the geometries of the native mitral (bicuspid valve) and tricuspid (three cusps) valves is significantly different, repairs of the tricuspid valve with mitral technologies has produced substandard long term results for patients with tricuspid disease. Therefore, there is a need for the development of annuloplasty devices tailored to the tricuspid valve geometry. Additionally, the annulus of the tricuspid valve is proximal to the AV Node of the heart in the triangle of Koch, a fundamental component of the electrical circuit of the heart. Suturing through this node, which can and happened during tricuspid repair causes heart block, complication which then needs to be addressed with a pacemaker. As a result there is a need for tricuspid annuloplasty devices that are optimally designed to the native tricuspid valve annular shape and which protect the AV node during implantation and prevents heart block. Finally, annuloplasty ring sizing on the tricuspid position is more complex than in the mitral position due to the lack of well-defined reference points in the tricuspid annulus. Therefore it would be of significant benefit to have a tricuspid annuloplasty device which can be adjusted in shape or size in order to improve patient outcome.

Despite multiple annuloplasty methods and devices currently on the market, there is a continued desire to improve such methods and devices. Particularly, there is a desire to have devices and methods that better accommodate the anatomy of the heart valve and the shape of the heart valve components throughout the cardiac cycle, and thereby improve results associated with valve repair surgery.

SUMMARY OF THE INVENTION

A tricuspid annuloplasty ring, configured for implantation in a tricuspid valve annulus, comprising a somewhat triangular shaped continuous body having an anterior segment, a septal segment and a posterior segment, wherein each of the anterior, septal and posterior segments are geometrically shaped from a three dimensional perspective to conform to the anatomic shape of the anterior, septal and posterior sections of the annulus of a tricuspid valve. Consistent with the anatomic shape of the sections of the annulus of a tricuspid valve, the segments of the annuloplasty ring vary in length and curvature when the ring segments are compared to each other, wherein the septal segment, which extends from a posterior-septal commissure to a anterior-septal commissure, is longer than the anterior segment and the anterior segment, which extends from the anterior-septal commissure to a anterior-posterior commissure, is longer than the posterior segment. The posterior segment extends from the anterior-posterior commissure to the posterior-septal commissure. In one embodiment, the septal segment of the annuloplasty ring is configured to reduce tension on tricuspid valve tissue and facilitate the elimination of a substantial portion of potential pressure or force that may be applied to the atrio-ventricular node by the annuloplasty ring upon its insertion. In another embodiment, at least one of the anterior, septal and posterior segments of the annuloplasty ring are configured to facilitate selective adjustment of a ring segment's respective length and shape. In one embodiment, adjustment of the length of one of the ring segments results in an adjustment of the angle between the remaining two ring segments, thereby causing an adjustment to the geometric characteristics of the ring. In another embodiment, adjustment of the length of one of the one of the ring segments results in an adjustment of the geometric shape of the ring segment adjusted.

BRIEF DESCRIPTION OF THE DRAWINGS

Non-limiting and non-exhaustive embodiments are described with reference to the following figures, wherein like reference numerals refer to like parts throughout the various views unless otherwise specified.

GENERAL DESCRIPTION OF THE INVENTION

Various embodiments are described more fully below with reference to the accompanying drawings, which form a part hereof, and which show specific embodiments of the invention. However, embodiments may be implemented in many different forms and should not be construed as limited to the embodiments set forth herein; rather, these embodiments are provided so that this disclosure will be thorough and complete, and will fully convey the scope of the invention to those skilled in the art. Accordingly, the following detailed description is, therefore, not to be taken in a limiting sense.

The present invention describes novel methods of heart valve repair and advanced embodiments of annuloplasty devices and delivery systems. The first type of the annuloplasty device is a somewhat triangular shaped non-planar ring made of a selected material which may be rigid, semi-flexible or flexible that is configured for implantation in a tricuspid valve annulus. It is further contemplated that the structure of the triangular shaped non-planar ring may range in stiffness on a continuum beginning with rigid and ending with flexible. In one embodiment, the ring can have completely rigid or flexible components but in another have a combination of rigid and flexible components that align with specific anatomical landmarks of the tricuspid annulus. In one embodiment, the triangular shaped ring is specifically configured for use with the annulus of a tricuspid valve, which is divided into three sections (septal, posterior and anterior segments) based on the position of the leaflets. The annular section of the tricuspid valve that holds the septal leaflet is called the septal section, the annular section that holds the anterior leaflet is called the anterior section and the annular section that holds the posterior leaflet is called the posterior section. The triangular shaped non-planar ring is divided into three segments, a septal segment, a posterior segment and an anterior segment. Each of these segments are geographically shaped to conform to the anatomic shape of the anterior, septal and posterior sections of the tricuspid valve annulus. Generally, each of the septal, posterior and anterior segments of the annuloplasty ring vary in length and curvature when compared to each other. In one embodiment, the septal segment of the annuloplasty ring is longer than the anterior segment of the annuloplasty ring and the anterior segment of the annuloplasty ring is longer than the posterior segment of the annuloplasty ring.

In another embodiment of the annuloplasty ring, the ring is configured to facilitate adjustment of its respective geometry so that it may better conform to the geometry of the annulus of the tricuspid valve of a specific patient. In this embodiment, the adjustment can be performed either during or after the surgery, using direct visual access and via biomedical imaging guided minimally invasive tools. In this embodiment, the acute angle between two adjacent segments of the triangular shaped ring may be changed by adjusting the length of the third opposite segment. For example, to reduce the acute angle between the septal and posterior segments of the annuloplasty ring the length of the anterior segment of the ring may be reduced. Alternatively, this adjustability of the angle between two adjacent segments of the ring facilitates independent control over individual leaflets and selective reduction of the dimension of the tricuspid annulus at specific locations along the annular circumference. Further independent control over individual leaflets is facilitated by modifying the shape of any one of these segments of the annuloplasty ring, caused by a changing of shape of at least the internal edge of a select segment of the ring.

Tricuspid regurgitation may be caused by lack of coaptation between all three of the leaflets or is frequently localized due to lack of coaptation of one of the leaflets with the other two due to the leaflet moving away from the other two leaflets. The adjustability of the geometry of the annuloplasty ring facilitates independent control over each leaflet, and will enable the manipulation of the geometry of the septal, posterior and anterior segments of the annulus of the tricuspid valve proximate to any one leaflet in order to move any leaflet causing a lack of coaptation back to its normal position with minimal perturbation of the other two leaflets. Once adjusted, the shape of the annuloplasty ring and or the length of a segment thereof may be fixed using a simple lock mechanism, allowing the surgeon to create and select a shape and size of the annuloplasty ring based on patient-specific tricuspid valve pathology.

In other embodiments of the invention, this device may be attached to a holder for surgical implantation. The holder comprises a long arm device used for implantation through small orifices, or an adjustable delivery system in which the annuloplasty ring is initially collapsed for minimally invasive delivery. The adjustable delivery system must have an internal cavity in which the ring may be initially collapsed. The system may or may not have steerable components in order to guide the system and take the ring to its implantation site. After reaching the implantation site, the ring is retrieved from the cavity, expanded and an attaching system is used to attach the ring to the annulus of the tricuspid valve guided by eco or other imaging modalities. The ring may be attached using sutures in an automatic system actuated by the user, clips, hooks or other sorts of anchoring components. The anchoring system then pulls the annulus in order for it to take the shape of the rings. The ring may then be actuated to reduce in size in order to correct regurgitation or may maintain the same dimension when used to simply stabilize the annulus. The ring is then detached from the delivery system and the delivery system is retracted from the patient's body. The type of devices will allow for surgical, beating heart or minimally invasive deployment.

The embodiments of the present invention as shown in the accompanying figures and described herein are particularly designed for or relate to the tricuspid valve. However, the present invention is not limited for application to the tricuspid valve, and it is contemplated that variations of the embodiments may apply to other heart valves, including but not limited to the bicuspid valve.

DETAILED DESCRIPTION OF EMBODIMENTS OF THE INVENTION DETAILED

Figure 2A:
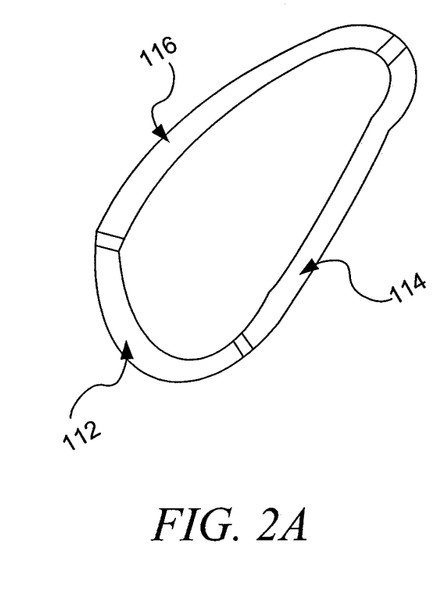
FIG. 2A is plan view of an example of an embodiment of an annuloplasty ring of the present invention.

Referring now to FIG. 2A, a first embodiment of the annuloplasty device 110 is comprised of a somewhat triangular shaped non-planar ring made of a selective material that could be either rigid, semi flexible or flexible that is configured for implantation in a tricuspid valve annulus. It is contemplated that the structure of the somewhat triangular shaped non-planar ring may be semi-rigid, flexible, or range in stiffness along a continuum beginning with rigid and ending with flexible. In the embodiment illustrated, the triangular shaped ring 110 is divided into three segments, a posterior segment 112, a septal segment 114, and an anterior segment 116. Each segment 112, 114, 116 of the triangular shaped ring 110 are geographically shaped to conform to the anatomic shape of the anterior, septal and posterior sections of a normal human tricuspid valve annulus or the annulus in a healthy patient. Generally, each of the posterior 112, septal 114 and anterior 116 segments of the annuloplasty ring 110 vary in length and curvature when compared to each other. In one embodiment, the septal segment 114 of the annuloplasty ring 110 is longer than the anterior 116 segment of the annuloplasty ring 110 and the anterior segment 116 of the annuloplasty ring 110 is longer than the posterior segment 112 of the annuloplasty ring 110. For example, in one embodiment of the invention, the length of the different segments of the triangular shaped non-planar ring 110 is defined by the mathematical relation: where the Septal 114 segment=1.5×Anterior 116 segment and the Anterior 116 segment=2×posterior segment 112.

This relationship has been established to be average for normal tricuspid human valves and is preserved across species. In one embodiment, the edge of the longest segment of the annuloplasty ring 110 is sutured onto the septal section of the annulus. In this embodiment, the longest segment of annuloplasty ring 110 is septal segment 114. The edge of the smaller segment is sutured onto the anterior section of the annulus. The smaller segment of the annuloplasty ring 110 is the anterior segment 116. The edge of the smallest segment is sutured onto the posterior section of the annulus. In this embodiment, the smallest segment of the annuloplasty ring 110 is the posterior segment 112.

The edges of each segment 112, 114, 116 of annuloplasty ring 110 have a curvilinear shape with a very large radius of curvature corresponding to the centroid of the annuloplasty ring 110. The radius of curvature of each of the edges 112, 114, 116 of annuloplasty ring 110 is different and is determined based on the native curvature of the anterior, septal and posterior sections of the tricuspid valve annulus. The septal segment 114 of annuloplasty ring 110 has the largest radius of curvature, followed by the anterior segment 116, with the posterior segment 112 having the smallest radius of curvature corresponding to the centroid. At the position of the atrio-ventricular node 20, along the septal segment 114 of annuloplasty ring 110 which would be sutured close to the atrio-ventricular node 20, in one embodiment, illustrated in FIG. 2B, the segment 114 will have a flat surface 118 which will come in contact with the wall of the heart in order to prevent perivalvular leakage while not necessitating suturing. In another embodiment, illustrated in FIG. 2C, a portion of septal section 114 is completely removed 138 from annuloplasty ring 110 in order to avoid imposing any pressure/force on the atrio-ventricular node 20 by ring 110 when it is positioned in the tricuspid valve annulus. When implanted, a first septal end 134 and a second septal end 136 of the annuloplasty ring 110 may be sutured to the septal portion of the annulus. The opening 138 created by removal of a portion of the septal section 114 facilitates the elimination of any potential pressure or force that may be applied to the atrio-ventricular node 20 by ring 110. The size of the opening between first septal end 134 and a second septal end 136 may be increased on decreased in other embodiments. In embodiments where additional support for ring 110 is required, a ring having a smaller opening between first septal end 134 and a second septal end 136 may be used. In embodiments where a smaller number of sutures is necessary to anchor the ring, and there is ambiguity surrounding the exact location of the atrio-ventricular node 20, a larger opening between first septal end 134 and a second septal end 136 may be used.

Figure 3:
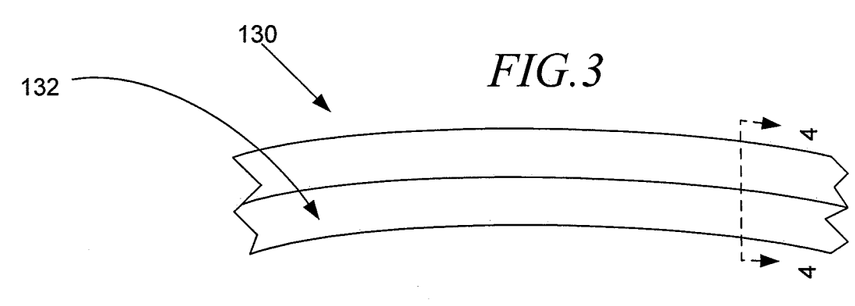
FIG. 3 is a bottom partial view of a portion of the septal segment of another embodiment of the annuloplasty ring illustrated in FIG. 2 wherein a portion of the septal segment that is positioned in proximity to AV node has been modified.
Figure 4:
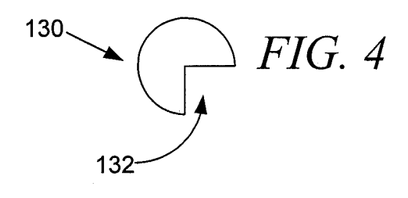
FIG. 4 is a sectional view along the portion of the septal segment illustrated in FIG. 12.

In another embodiment, illustrated in FIGS. 3 and 4, a portion 132 of a section 130 of annuloplasty ring 110 is removed to create a notch in the internal structure of the septal section of the ring. The portion of the septal section includes a notch in order to avoid imposing any pressure/force on the atrio-ventricular node 20 by the annuloplasty ring 110 when it is positioned in the tricuspid valve annulus. It is contemplated that the notch created by the removal of a section of a portion of the annuloplasty ring 110 that may be positioned in proximity to the atrio-ventricular node 20 when the annuloplasty ring 110 is positioned in the tricuspid valve annulus may take on a plurality of shapes and sizes, so long as the septal section 114 of the ring 110 is of one piece and prevents longitudinal movement.

Figure 5:
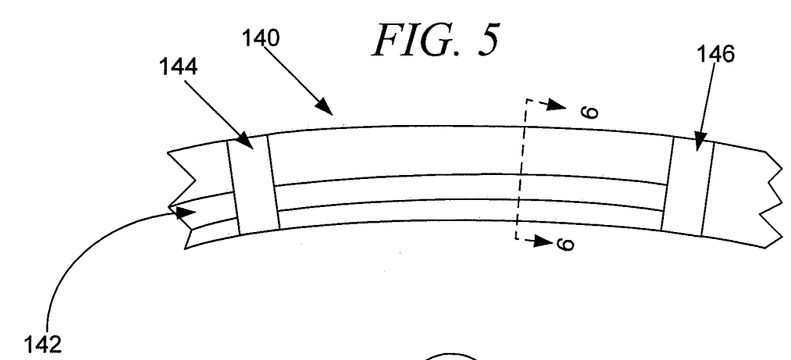
FIG. 5 is a bottom partial view of a portion of the septal segment of another embodiment of the annuloplasty ring illustrated in FIG. 2 wherein a portion of the septal segment that is positioned in proximity to AV node has been modified.
Figure 6:
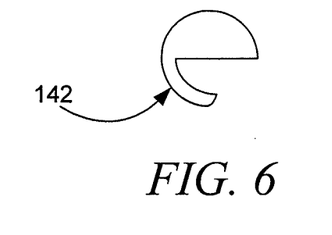
FIG. 6 is a sectional view along the portion of the septal segment illustrated in FIG. 12.

FIGS. 5 and 6 illustrate another embodiment of annuloplasty ring 110, whereby a first free end 134 and a second free end 136 are connected by a bridge 140. The bridge is configured to reduce possible tension on tissue around the atrio-ventricular node 20 that normally would be applied by the segment of the annuloplasty ring 110 in embodiments when ring 110 is configured without any removal of parts or ports of the septal segment. In the embodiment illustrated, bridge 140 is comprised of a first bridge end 144 and a second bridge in 146 connected by a strut 142. In this embodiment, the imposition of pressure/force on the atrio-ventricular node 20 is removed or alleviated by the bridged structure 140 that connects the first free end 134 and a second free end 136 of annuloplasty ring 110.

Figure 2B:
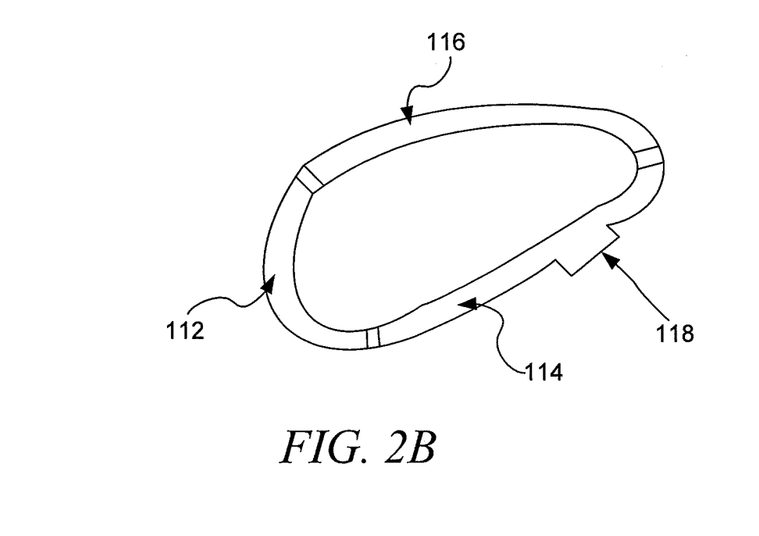
FIG. 2B is plan view of an example of another embodiment of an example of an annuloplasty ring of the present invention.
Figure 2C:
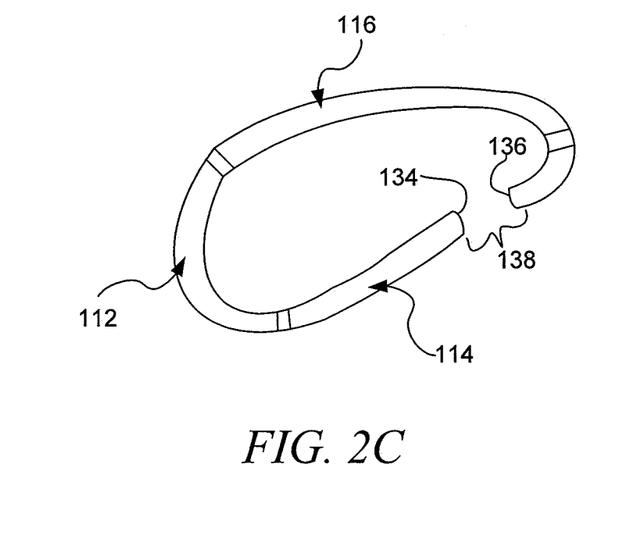
FIG. 2C is plan view of an example of another embodiment of an example of an annuloplasty ring of the present invention.

The annuloplasty ring 110 described in FIGS. 2A-2C, is has a curvature out of the plane of the ring 110, forming a saddle shape that conforms to the native saddle shape of a normal human tricuspid annulus. The saddle curvature associated with each segment of the annuloplasty ring 110, as illustrated in FIG. 2A, varies in relation to each other in order to conform to the normal shape of tricuspid valves. It is contemplated that saddle curvatures for the annuloplasty ring may be 0-10% for the anterior segment 116, and posterior segment 112 and 0-20% septal segment 114. As one of ordinary skill in the art may understand in an additional embodiment, an average saddle curvature for each of the annuloplasty ring 110 segments 112, 114, 116 may be appropriate in some cases.

Figures 7, 8, 9, 10, 11:
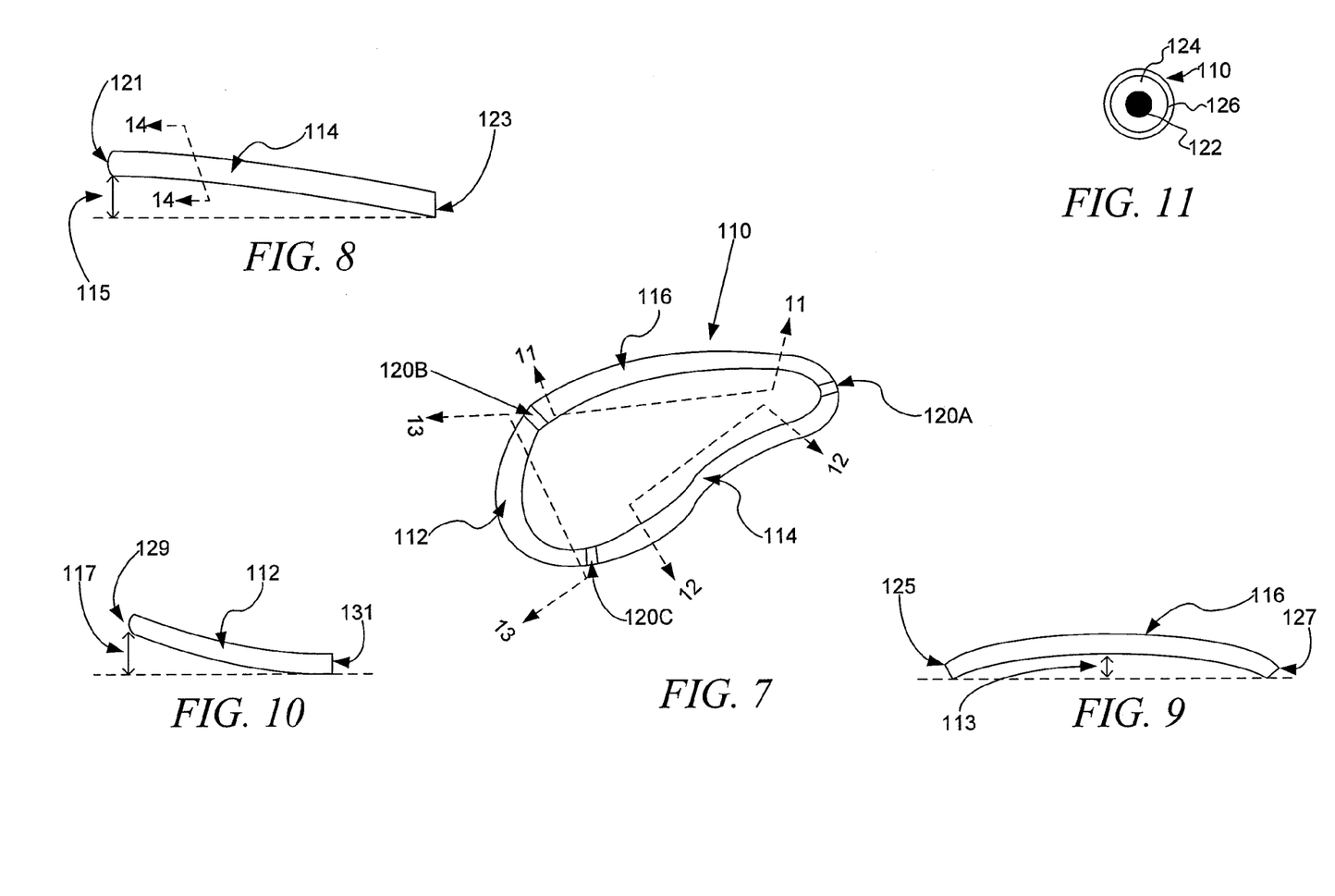
FIG. 7 is a top view of an example of an embodiment of an annuloplasty ring of the present invention.
FIG. 8 is a partial view of the septal segment of an example of an annuloplasty ring of the present invention.
FIG. 9 is a partial view of the anterior segment of an example of an annuloplasty ring of the present invention.
FIG. 10 is a partial view of the posterior segment of an example of an annuloplasty ring of the present invention.
FIG. 11 is a sectional view along the anterior segment of an example of an annuloplasty ring of the present invention.

FIG. 7 illustrates a top view of annuloplasty ring 110, illustrating the posterior segment 112, anterior segment 114, and septal segment 116 each segment of which is connected by a rigid connecting structure 120A, 120B, and 120C. FIGS. 8, 9, and 10 illustrate the three dimensional aspects of the posterior 112, anterior 116, and septal 114 segments of annuloplasty ring 110. FIG. 8 is a side view of annuloplasty ring 110, illustrating ring 110 from the perspective of the septal segment 114 and thereby illustrating the three dimensional aspects of ring 1110, showing a first end 121 of septal segment 114, which is positioned at the septal posterior commissure when annuloplasty ring 110 is positioned in the tricuspid valve annulus, is at a higher plane than a second end 123 of septal segment 114. The second end 123 of septal segment 114, which is positioned at the septal anterior commissure when annuloplasty ring 110 is positioned in the tricuspid valve annulus, is positioned at a lower plane than the first end 121 of septal segment 114. Arrow 115 is representative of the longitudinal difference between the highest point 121 and the lowest point of septal segment 114. FIG. 9 is a side view of annuloplasty ring 110, illustrating ring 110 from the perspective of the anterior segment 116 and thereby illustrating its three dimensional aspects, showing that a first end 125 of anterior segment 116, which is positioned at the anterior posterior commissure when annuloplasty ring 110 is positioned in the tricuspid valve annulus, is on the same plane as a second end 127 of anterior segment 116. The highest point on anterior segment 116, referenced by arrow 113, is towards the middle of the anterior segment 116. The second end 127 of anterior segment 116 is positioned at the anterior septal commissure when annuloplasty ring 110 is positioned in the tricuspid valve annulus. FIG. 10 is a side view of annuloplasty ring 110, illustrating ring 110 from the perspective of the posterior segment 112 and thereby illustrating its three dimensional aspects, showing a first end 129 of posterior segment 112, which is positioned at the posterior anterior commissure when annuloplasty ring 110 is positioned in the tricuspid valve annulus, is at a higher plane than a second end 129 of posterior segment 112. The second end 131 of posterior segment 112, which is positioned at the posterior septal commissure when annuloplasty ring 110 is positioned in the tricuspid valve annulus, is positioned at a lower plane than the first end 129 of septal segment 114. Arrow 117 is representative of the longitudinal difference between the highest point 129 and the lowest point of posterior segment 112.

FIG. 11 is a cross sectional view illustrating an embodiment of the materials that comprise annuloplasty ring 110, which may be comprised of an inner core of structural support 122, a protective cover 124 and an exterior surface 126. The inner core of structural support 122 may be comprised of a metal such as titanium wire rope. The inner core of structural support 122 is embedded into a molded silicone tube 124 and made into a desired shape. The silicone 124 is then covered by a suturing cuff 126 made from a biocompatible material. It is contemplated that the inner structural support of the annuloplasty ring 110 may be constructed from a plurality of different metals, polymers ceramics or other materials without altering the basic concept or function of the device. It is further contemplated that the material of the inner structural support 122 may be comprised of rigid, semi-rigid or flexible material, thereby allowing for a plurality of embodiments illustrating a plurality of levels of rigidity in annuloplasty ring 110. It is also contemplated that rigidness of annuloplasty ring 110 may be modified by changing the shape and size of inner structural support 122. In other embodiments, inner structural support 122 may be made thinner. In other embodiments, inner structural support 122 may be made more flat. Whether by way of modifying the rigidity of or flattening inner structural support 122, it is contemplated that the rigidness of the annuloplasty ring 110 may range from being extremely rigid down to extremely flexible. It is contemplated that the flexibility in some embodiments may be such that the shape of annuloplasty ring 110 is responsive to the forces applied by the walls of the heart.

Figure 12:
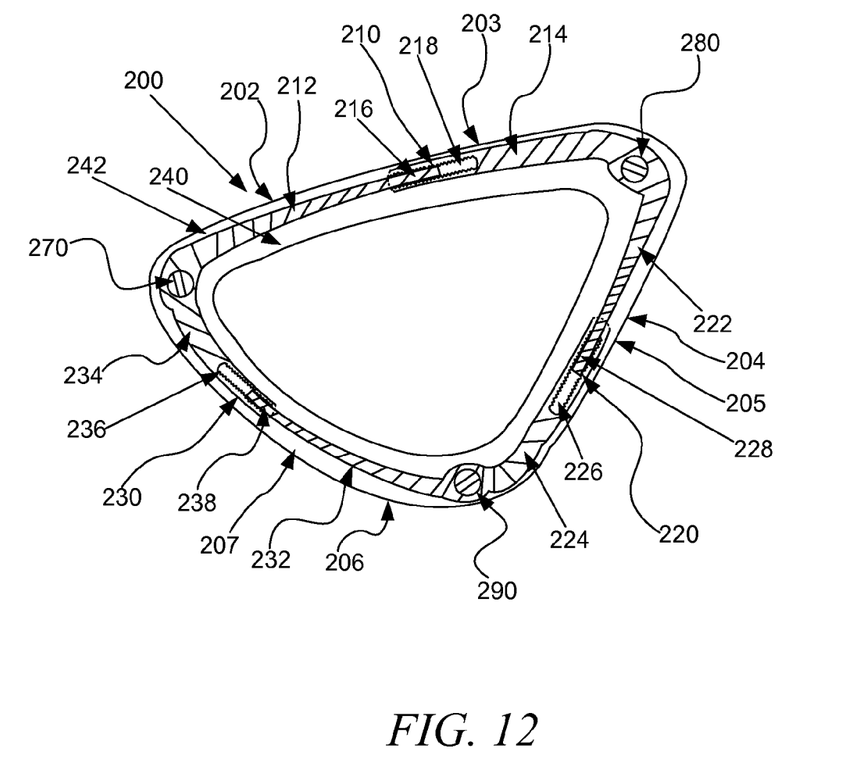
FIG. 12 is a top sectional view of another embodiment of an annuloplasty ring of the present invention, illustrating the length adjustment mechanism that may reside in each section of the ring.

In another embodiment of the annuloplasty ring illustrated in FIG. 12, the ring 200 is configured to facilitate adjustment of the size of each of the three segments 202, 204, 206, of ring 200 resulting in a change in the respective geometry of the ring so that it may better conform to the geometry of the annulus of the tricuspid valve of a specific patient after implantation in the heart. In this embodiment illustrated, the acute angle between two adjacent segments of the triangular shaped ring 200 can be changed by adjusting the length of the third opposite segment. For example, to reduce the acute angle between anterior segment 202 and septal segment 204 of the ring 160, the length of posterior segment 206 may be reduced. Alternatively, the adjustability of the length of anterior segment 202, septal segment 204 and posterior segment 206 facilitates independent control over individual leaflets.

Anterior segment 202 is comprised of an inner arm core 210 and outer layer 203. The inner arm core 210 is comprised of an anterior first sub-segment 212, having an orifice at one end through which a first connector 270 of a first gearbox (shown in FIG. 13) is inserted, and an anterior second sub-segment 214 having an orifice at one end through which a second connector 280 of a second gearbox (shown in FIG. 13) is inserted. At the second end of anterior first sub-segment 212, anterior first sub-segment 212 has a threaded male portion 216 configured and sized for insertion into a threaded female hollow portion 218 on a second end of anterior second sub-segment 214. The threaded male portion 216 of the anterior first sub-segment 212 may be screwed into the threaded female hollow portion 218 configured on the second end of anterior second sub-segment 214 by engaging the first connector 270 of the first gearbox, thereby increasing or decreasing the length of anterior segment 202.

Septal segment 204 is comprised of an inner arm core 220 and outer layer 205. The inner arm core 220 is comprised of a septal first sub-segment 222, having an orifice at one end through which a second connector 280 of a second gearbox (shown in FIG. 13) is inserted, and a septal second sub-segment 224 having an orifice at one end through which a third connector 290 of a third gearbox (shown in FIG. 13) is inserted. At the second end of septal first sub-segment 222, septal first sub-segment 222 has a threaded male portion configured and sized for insertion into threaded female hollow portion 226 configured the second end of septal second sub-segment 224. The threaded male portion 228 of the septal first sub-segment 222 may be screwed into the threaded female hollow portion 226 configured on the second end of septal second sub-segment 224 by engaging the second connector 280 of the second gearbox, thereby increasing or decreasing the length of septal segment 204.

Posterior segment 206 is comprised of an inner arm core 230 and outer layer 207. The inner arm core 230 is comprised of a posterior first sub-segment 232, having an orifice at one end through which a third connector 290 of a third gearbox (shown in FIG. 13) is inserted, and a posterior second sub-segment 234 having an orifice at one end through which a first connector 270 of a first gearbox (shown in FIG. 13) is inserted. At the second end of posterior first sub-segment 232, posterior first sub-segment 232 has a threaded male portion 238 configured and sized for insertion into a threaded female hollow portion 236 configured on the second end of posterior second sub-segment 234. The threaded male portion 238 of the posterior first sub-segment 232 may be screwed into the threaded female hollow portion 236 configured on the second end of posterior second sub-segment 234 by engaging the third connector 290 of the third gearbox, thereby increasing or decreasing the length of third segment 206.

Figure 13:
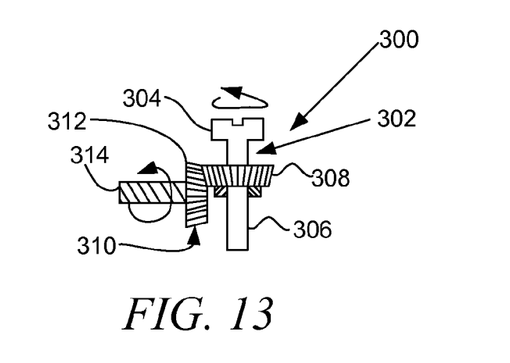
FIG. 13 is an illustration of the gear box that facilitates geometric and size adjustments mechanism that may be performed on each section of another embodiment of the annuloplasty ring.
Figure 14:
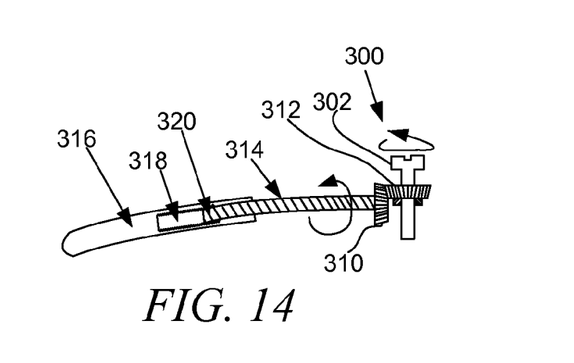
FIG. 14 is an illustration of the gear box operatively connected to a adjustable leg portion of a section of the annuloplasty ring illustrated in FIG. 15.

As illustrated in FIG. 13, gear box 300 is comprised of a first connector 302 having a head 304 and rod 306 portions, wherein the head portion 304 is configured for being engaged by at least a flat screwdriver in order to rotate the rod portion 306 and thereby a first gear wheel 308 attached to the rod portion 306. The first gear wheel 308 engages a second gear wheel 312 of a second connector 310 and thereby a second rod portion 314 which when extended serves as an inner arm core of the first, second and third segments. As illustrated in FIG. 14, a first end 320 of inner arm core 314 has a threaded male portion 320 configured and sized for insertion into a threaded female hollow portion 318 configured on the second end of second segment 316. The threaded male portion 320 of inner arm core 314 may be screwed into the threaded female hollow portion 318 configured on the second end of second segment 316 by rotatingly engaging the first connector 302 of third gearbox 300, thereby increasing or decreasing the length of the inner core arm.

Figure 15:
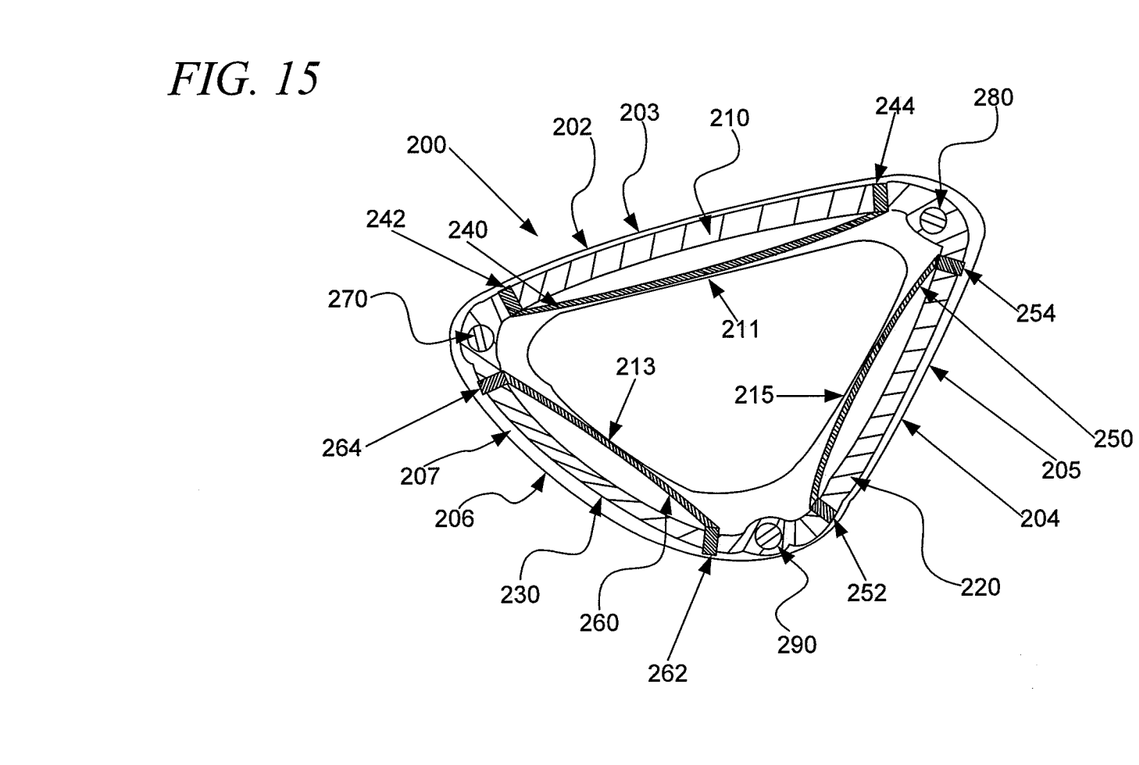
FIG. 15 is a top sectional view of another embodiment of an annuloplasty ring of the present invention, illustrating the shape adjustment mechanism that may reside in each section of another embodiment of the annuloplasty ring.

In another embodiment of the annuloplasty ring 200 illustrated in FIG. 15, the ring 200 is configured to facilitate modification of the geometry of each of the three segments 202, 204, 206, of ring 200 resulting in a change in the respective geometry of the ring so that it may better conform to the geometry of the annulus of the tricuspid valve of a specific patient. Tricuspid regurgitation may be caused due to a lack of coaptation between all three of the tricuspid valve leaflets. In some circumstances, the cause of regurgitation is localized due to a lack of coaptation of one of the leaflets with the other two as a result of one leaflet moving away from the other two leaflets. The adjustability of the geometry of the annuloplasty ring 200 facilitates independent control over each leaflet, and will enable the manipulation of the geometry of the septal, posterior and anterior segments of the annulus of the tricuspid valve proximate any one leaflet in order to move any leaflet, causing a lack of coaptation, back to an acceptable position with minimal perturbation of the other two leaflets. Once adjusted, the shape of a segment of annuloplasty ring 200 may be fixed using a simple lock mechanism, allowing the surgeon to create and select an optimal geometric shape of the annuloplasty ring 200 based on patient-specific tricuspid valve pathology.

In the embodiment illustrated in FIG. 15 illustrates, each of the anterior 202, septal 204 and posterior 206 segments may include an internal assembly that allow for adjustment of the shape of a segment 202, 204, 206. The anterior segment 202 includes an adjustable arm 240 attached to an internal leg 210 by first and second connecting clamps 242, 244. Upon the adjustment of arm 240, the interior edge 211 of the anterior segment 202 is modified, thereby changing the shape of anterior segment 202. It is contemplated that the engagement mechanism for adjusting arm 240 is a gearbox 270. Alternatively, the mechanism for adjusting arm 240 may be a torsion or spring assembly. In addition, the adjustment mechanism may include a locking mechanism that locks arm 240 in respective position in order to stabilize the geometry of the anterior segment 202 once an optimal geometric shape has been determined by a physician.

Regarding the septal segment 204, it includes an adjustable arm 250 attached to an internal leg 220 by first and second connecting clamps 252, 254. Upon the adjustment of arm 250, the interior edge 215 of the septal segment 204 is modified, thereby changing the shape of septal segment 204. It is contemplated that the engagement mechanism for adjusting arm 250 is a gearbox 280. Alternatively, the mechanism for adjusting arm 250 may be a torsion or spring assembly. In addition, the adjustment mechanism may include a locking mechanism that locks arm 250 in a respective position in order to stabilize the geometry of the septal segment 204 once an optimal geometric shape has been determined by a physician.

Regarding the posterior segment 206, it includes an adjustable arm 260 attached to an internal leg 230 by first and second connecting clamps 262, 264. Upon the adjustment of arm 260, the interior edge 213 of the posterior segment 206 is modified, thereby changing the shape of posterior segment 206. It is contemplated that the engagement mechanism for adjusting arm 260 is a gearbox 290. Alternatively, the mechanism for adjusting arm 260 may be a torsion or spring assembly. In addition, the adjustment mechanism may include a locking mechanism that locks arm 260 in a respective position in order to stabilize the geometry of the posterior segment 206 once an optimal geometric shape has been determined by a physician.

Figure 16:
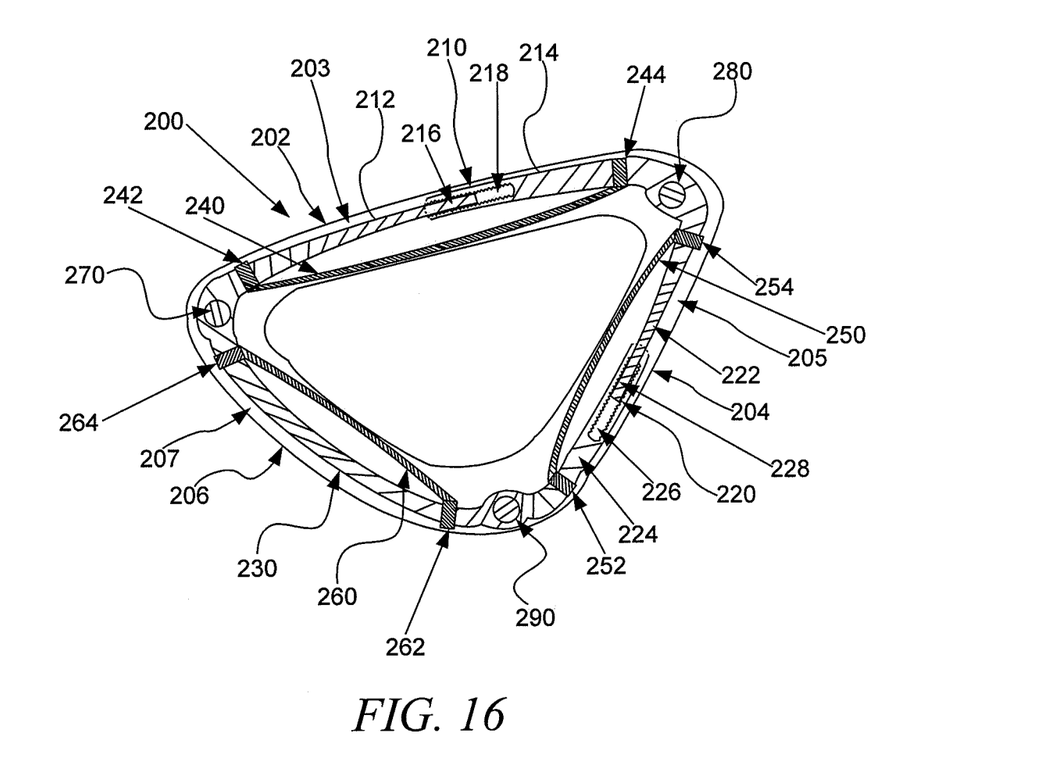
FIG. 16 is a top sectional view of another embodiment of an annuloplasty ring of the present invention, illustrating the length and shape adjustment mechanisms that may reside in each section of another embodiment of the annuloplasty ring.
Figure 17:
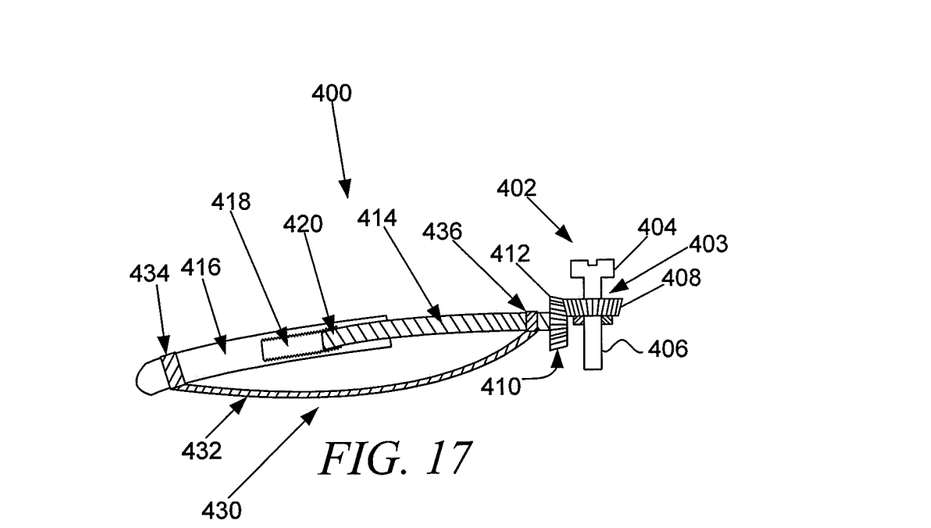
FIG. 17 is an illustration of the gear box operatively connected to a leg portion including length and shape adjustment mechanisms within a section of the annuloplasty ring illustrated in FIG. 19.

In another embodiment of the annuloplasty ring illustrated in FIG. 16, annuloplasty ring 200 is configured to facilitate adjustment of the size of each of the three segments 202, 204, 206, of ring 200 and the respective geometry of the ring so that it may better conform to the geometry of the annulus of the tricuspid valve of a specific patient after implantation in the heart. FIG. 16 is a combination of the ring 200 illustrated in FIGS. 12 and 18 and the respective components ring 200, including the assembly to change the size of each segment and the assembly to modify the geometry of each segment function as set forth above regarding FIGS. 12 and 16. FIG. 17 is an illustration of the assembly 400 which performs the function of adjusting the size of each of the three segments 202, 204, 206, of ring 200 and the respective geometry of the ring 200. As illustrated, a gear box 402 is comprised of a first connector 403 having a head 404 and rod 406 portions, wherein the head portion 404 is configured for being engaged by at least a flat screwdriver in order to rotate the rod portion 406 and thereby a first gear wheel 408 attached to the rod portion 406. The first gear wheel 408 engages a second gear wheel 412 of a second connector 410 and thereby a second rod portion 414 which when extended serves as an inner arm core of the anterior 202, septal 204 and posterior 206 segments illustrated in FIG. 16. As illustrated in FIG. 17, a first end of inner arm core 414 has a threaded male portion 420 configured and sized for insertion into a threaded female hollow portion 418 configured on the second end of second segment 416. The threaded male portion 420 of inner arm core 414 may be screwed into the threaded female hollow portion 418 configured on the second end of second segment 416 by rotatingly engaging the first connector 402, thereby increasing or decreasing the length of the inner core arm. As illustrated, adjustable arm 432 is attached to second segment 416 and inner arm core 414. Upon adjustment of the size of the inner core arm, when the adjustable arm 432 is permanently attached to second segment 416 and inner arm core 414 by connecting clamps 433, 436. Upon the adjustment of the size of the inner core arm, for when the size of the arm is lessened, this causes the adjustable arm 432 to bow outward toward the center of the ring, thereby changing the geometry of the interior edge of a select segment of the ring and thereby changing the shape of the segment into which assembly 400 is configured. It is contemplated that the engagement mechanism for adjusting arm 432 is a gearbox 402. Alternatively, the mechanism for adjusting arm 432 may be a torsion or spring assembly. In addition, the adjustment mechanism may include a locking mechanism that locks arm 432 in a respective position in order to stabilize the geometry of a segment once an optimal geometric shape has been determined by a physician.

Figure 18A:
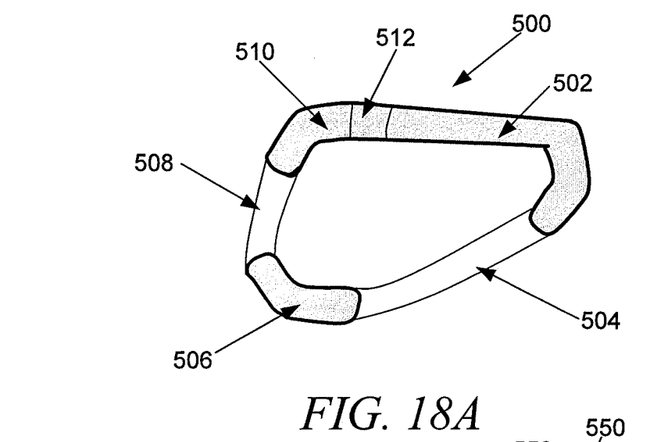
FIG. 18A is plan view of an example of another embodiment of an example of an annuloplasty ring of the present invention.
Figure 18B:
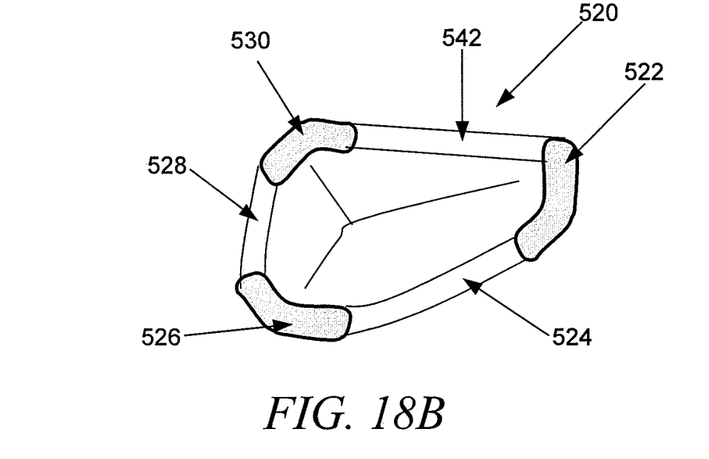
FIG. 18B is plan view of an example of another embodiment of an example of an annuloplasty ring of the present invention.

As previously set forth, it is contemplated that the structure of the triangular shaped non-planar ring may range in stiffness on a continuum beginning with rigid and ending with flexible. It is further contemplated that different segments of the annuloplasty ring may be comprised of varying stiffness. Referring to FIG. 18A, an embodiment of the annuloplasty device 500 is shown illustrating a somewhat triangular shaped non-planar semi-rigid ring. In the embodiment illustrated, the triangular shaped ring 500 is comprised of a rigid septal segment 502, a flexible anterior segment 504, a rigid antero-posterior short segment 506, a flexible posterior segment 508, a rigid postero-septal segment 510 and a detachable atrial segment 512 that is positioned near the atrial node 20 when the ring 500 is inserted into the annulus of a valve. In another embodiment illustrated in FIG. 18B, the triangular shaped ring 520 is comprised of a rigid septal-anterior segment 522, a flexible anterior segment 524, a rigid antero-posterior segment 526, a flexible posterior segment 528, a rigid postero-septal segment and a flexible septal segment 542.

Figure 19:
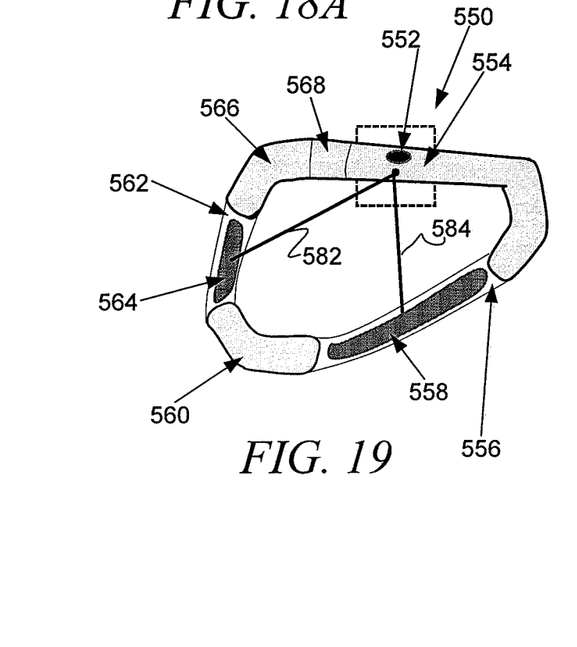
FIG. 19 is plan view of an example of another embodiment of an example of an annuloplasty ring of the present invention.
Figure 20:
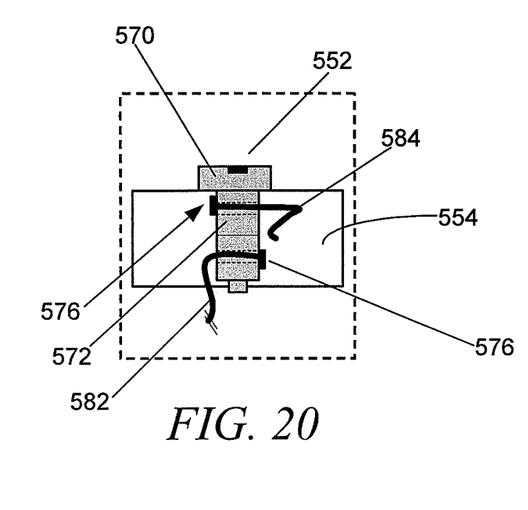
FIG. 20 is an illustration of the gear box operatively connected to an adjustable leg portion of a section of the annuloplasty ring illustrated in FIG. 19.

FIG. 19 illustrated another embodiment of a semi-rigid adjustable annuloplasty ring configured for shape adjustment. As illustrated, the annuloplasty device 550 is shown illustrating a somewhat triangular shaped non-planar semi-rigid ring comprised of a rigid septal segment 554, a flexible anterior segment 556, a deflectable anterior inner arm portion 558, a rigid antero-posterior 560, a flexible posterior segment 562, a deflectable posterior inner arm portion 564, a rigid postero-septal segment 566 and a detachable sinus node segment 568 that is positioned near the atrial node 20 when the ring 550 is inserted into the annulus of a valve. A gearbox 552 is configured within rigid septal segment 554 and includes first and second flexible wires 582, 584 connecting the gearbox 552 and the deflectable anterior inner arm portion 558 and the deflectable posterior inner arm portion 564. As illustrated in FIG. 20, the gearbox 552 is comprised of a rotatable gear head attached to a shaft 572. Shaft 572 includes a first orifice through which first flexible wire 582 extends and is operatively held in place by a first stopper 576 and a second orifice through which second flexible wire 584 extends and is operatively held in place by a second stopper 578. During operation when gearbox 552 is engaged, shaft 572 rotates causing first and second flexible wires 582, 584 to shorten by wrapping around the shaft 572 and thereby exerting force on the deflectable anterior inner arm portion 558 and the deflectable posterior inner arm portion 564, thereby reducing the linear dimension from the gear box 552 to the inner deflectable anterior arm 564 and inner deflectable posterior arm 558. In addition, the force exerted on the deflectable anterior inner arm portion 558 and the deflectable posterior inner arm portion 564 modifies the shape of flexible anterior segment 556 and flexible posterior segment 562. In another embodiment of this device, shaft 572 may be divided into two halves, an upper half and a lower half. When gearbox 552 is engaged, the upper half of shaft 572 turns and thereby causes flexible wire 582 to shorten. Also, when gearbox 552 is engaged the lower half of shaft 572 turns, causing flexible wire 584 to shorten. It is contemplated that each of flexible wires 582 and 584 may be shortened either independently or together upon engagement of gearbox 552. Upon adjusting flexible wires 582 and 584 to the desired lengths, the gear box may be locked to retain the final shape of anterior inner arm portion 558 and posterior inner arm portion 564 obtained after adjustment. The rotatable gear head consists of a groove into which an adjustment screw driver may be inserted and turned to adjust the lengths of the flexible wire members 582 and 584.

In another embodiment of the annuloplasty ring, each segment of the triangular shaped ring has an L-shape with the longer arm of the L curved. The shorter segment of the L has a smaller diameter compared to the larger segment and inserts into the end of the longer segment of the L-shaped segment adjacent to it, i.e., the smaller arm of the L-shaped septal segment inserts into the end of the longer arm of the posterior segment, the smaller arm of the L-shaped posterior segment inserts into the end of the longer arm of the anterior segment and the smaller arm of the anterior segment inserts into the longer arm of the septal segment respectively. The segments of the annuloplasty ring are made independently into three different components, and then assembled together by inserting one edge into another as described above. Each of the septal, posterior and anterior segments of the ring are comprised of an inner core of metal, such as titanium wire rope and embedded into a molded silicone tube made into a desired shape. The diameters of the segments are calculated such that when assembled together, the assembly forms a somewhat triangular shaped ring. The segment of the ring at the site of the atrio-ventricular node 20 has a notch going inwards into the ring created by removing some material from the ring. The space created by removing the material from the ring is filled with a soft material that restricts applying any force onto the atrio-ventricular node 20 by the ring. To those skilled in the art it is obvious that changing the angle between two of the ring's septal, posterior and anterior segments is not restricted to mechanical systems that change the length of the third segment. Different mechanical systems bases on gears, pulleys and torsion springs among other may facilitate a change in the angle between two of the ring's septal, posterior and anterior segments with or without changing the length of the third. In the embodiment in which the length of the third segment doesn't change in length, the different segment must deform in order to accommodate for the new geometry.

In other embodiments of the tricuspid annuloplasty ring, the inner structure may have dimension or be constructed from materials which may render the device as a whole as that defined in the clinical practice as semi-flexible or flexible. Additional heterogeneous inner structure materials or treatment of the material may be used to have varying levels of rigidity of the ring throughout its perimeter.

Reference may be made throughout this specification to "one embodiment," "an embodiment," "embodiments," "an aspect," or "aspects" meaning that a particular described feature, structure, or characteristic may be included in at least one embodiment of the present invention. Thus, usage of such phrases may refer to more than just one embodiment or aspect. In addition, the described features, structures, or characteristics may be combined in any suitable manner in one or more embodiments or aspects. Furthermore, reference to a single item may mean a single item or a plurality of items, just as reference to a plurality of items may mean a single item. Moreover, use of the term "and" when incorporated into a list is intended to imply that all the elements of the list, a single item of the list, or any combination of items in the list has been contemplated.

One skilled in the relevant art may recognize, however, that the invention may be practiced without one or more of the specific details, or with other methods, resources, materials, etc. In other instances, well known structures, resources, or operations have not been shown or described in detail merely to avoid obscuring aspects of the invention.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

The above specification, examples and data provide a description of the manufacture and use of the invention. Since many embodiments of the invention can be made without departing from the spirit and scope of the invention, the invention resides in the claims hereinafter appended.

We claim:

1. A tricuspid annuloplasty ring configured for implantation in a tricuspid valve annulus having an anterior annulus section, a septal annulus section and a posterior annulus section, the annuloplasty ring comprising:

a triangular shaped continuous body having an anterior segment, a septal segment and a posterior segment, wherein each of the anterior, septal and posterior segments are geometrically shaped to conform to the anatomic shape of the anterior, septal and posterior sections of tricuspid valve annulus, wherein at least one of the anterior segment, the septal segment, and the posterior segment comprises a plurality of sub-segments, wherein a one of the plurality of sub-segments is detachable to create a triangular shaped discontinuous body to facilitate implantation, the triangular shaped continuous body having a first connection between the anterior segment and the septal segment, a second connection between the septal segment and the posterior segment, and a third connection between the anterior segment and the posterior segment, triangular shaped continuous body being flexible at at least one of the first connection, the second connection, and the third connection and rigid elsewhere, wherein the ring further comprises an adjustment device attached to the ring, wherein the adjustment device comprises:

a gearbox; and at least one flexible wire, wherein the at least one flexible wire connects the gearbox to the at least one of the flexible connections.

2. The tricuspid annuloplasty ring of claim 1 wherein the anterior, septal and posterior segments of the annuloplasty ring vary in length and curvature when compared to each other.

3. The tricuspid annuloplasty ring of claim 2 wherein the septal segment of the annuloplasty ring is longer than the posterior segment of the annuloplasty ring and the anterior segment of the annuloplasty ring is longer than the posterior segment of the annuloplasty ring.

4. The tricuspid annuloplasty ring of claim 3 wherein the septal segment extends from a posterior-septal commissure to an anterior-septal commissure, the anterior segment extends from the anterior-septal commissure to an anterior-posterior commissure and the posterior segment extends from the anterior-posterior commissure to the posterior-septal commissure.

5. The tricuspid annuloplasty ring of claim 1 wherein the annuloplasty ring has a defined edge comprising an optimal geometric configuration of exterior portions of the anterior, septal and posterior segments.

6. The tricuspid annuloplasty ring of claim 1 wherein a curvature of the anterior segment of the annuloplasty ring is greater than the curvature of the septal and posterior segments of the annuloplasty ring, wherein:

a two lowest points of the anterior segment are located at a posterior-septal commissure of the tricuspid valve and an anterior-septal commissure of the tricuspid valve; and a zenith of the ring is midway between the two lowest points on the anterior segment.

7. The tricuspid annuloplasty ring of claim 1 wherein the septal segment is configured such that a lowest point of the septal segment corresponds to the septal-anterior commissure and a highest point of the septal segment corresponds to the anterior-posterior commissure.

8. The tricuspid annuloplasty ring of claim 1 wherein the posterior segment is configured such that the lowest point on the posterior segment corresponds to a septal-posterior commissure and the highest point on the posterior segment corresponds to an anterior-posterior commissure.

9. The tricuspid annuloplasty ring of claim 1 has an inner circumferential shape such that projection of the ring onto a planar surface depicts a scalar triangle with unequal edges, wherein the geometric shape of the septal segment of the ring corresponds to the geometric shape of the septal segment of the tricuspid valve annulus, the geometric shape of the anterior segment of the ring corresponds to the geometric shape of the anterior segment of the tricuspid valve annulus and the geometric shape of the posterior segment of the ring corresponds to the geometric shape of the posterior segment of the tricuspid valve annulus.

10. The tricuspid annuloplasty ring of claim 1 wherein the at least one of the plurality of flexible segments comprises molded silicone and the at least one of the plurality of rigid segments comprises metal.

11. The tricuspid annuloplasty ring of claim 1, wherein the gearbox comprises a rotatable shaft connected to the at least one flexible wire, wherein actuating the gearbox rotates the shaft and adjusts a length of the at least one flexible wire between the shaft and the at least one of the flexible connections, such that an adjusted length of the at least one flexible wire initiates a deflection in the at least one of the flexible connections.

12. The tricuspid annuloplasty ring of claim 11, wherein the at least one of the flexible connections is a fixed length.

* * * * *